(12) United States Patent
Rubinstenn et al.

(10) Patent No.: US 7,008,929 B2
(45) Date of Patent: Mar. 7, 2006

(54) SAPOGENIN-BASED TREATMENT

(75) Inventors: Gilles Rubinstenn, Paris (FR); Bruno Buan, Bagnolet (FR)

(73) Assignee: L'Oreal, Paris (FR)

( * ) Notice: Subject to any disclaimer, the term of this patent is extended or adjusted under 35 U.S.C. 154(b) by 175 days.

(21) Appl. No.: 10/393,989

(22) Filed: Mar. 24, 2003

(65) Prior Publication Data

US 2003/0216327 A1    Nov. 20, 2003

Related U.S. Application Data

(60) Provisional application No. 60/374,159, filed on Apr. 22, 2002.

(30) Foreign Application Priority Data

Apr. 2, 2002  (FR)  .................................. 02 04072

(51) Int. Cl.
*A61K 31/704* (2006.01)
(52) U.S. Cl. .......................................... 514/26; 514/33
(58) Field of Classification Search ................ 514/26, 514/33
See application file for complete search history.

(56) References Cited

U.S. PATENT DOCUMENTS

| | | | |
|---|---|---|---|
| 5,607,693 | A | 3/1997 | Bonte et al. |
| 5,723,149 | A | 3/1998 | Bonte et al. |
| 6,294,157 | B1 | 9/2001 | Rubinstenn et al. |
| 6,331,535 | B1 | 12/2001 | Tuloup et al. |
| 6,528,043 | B1 | 3/2003 | Rubinstenn et al. |
| 2002/0028186 | A1 | 3/2002 | Rubinstenn et al. |
| 2004/0005370 | A1 | 1/2004 | Breton |
| 2004/0028757 | A1 | 2/2004 | Cals-Grierson, et al. |

FOREIGN PATENT DOCUMENTS

FR    2813194    *   3/2002

* cited by examiner

*Primary Examiner*—James O. Wilson
*Assistant Examiner*—Ganapathy Krishnan
(74) *Attorney, Agent, or Firm*—Oblon, Spivak, McClelland, Maier & Neustadt, P.C.

(57) ABSTRACT

The present invention relates to the use of a sapogenin, chosen from diosgenin and hecogenin, and/or of a plant extract containing at least one of these sapogenins. A preferred use is the treatment of oligoseborrheic dry skin. Another preferred use is the treatment of dry scalp. Compositions containing these sapogenins are also described.

10 Claims, No Drawings

SAPOGENIN-BASED TREATMENT

REFERENCE TO PRIOR APPLICATIONS

This application claims priority to U.S. provisional application 60/374,159, filed Apr. 22, 2002, and to French patent application 0204072 filed Apr. 2, 2002, both of which are incorporated herein by reference.

FIELD OF THE INVENTION

The present invention relates to the use of a sapogenin chosen from diosgenin and hecogenin (including a mixture thereof), and/or of a plant extract containing one or both of these specific sapogenins. A preferred use is the treatment of oligoseborrheic dry skin. Another preferred use is the treatment of dry scalp. Compositions containing these sapogenins are also described.

The sapogenin and composition thereof may be used for cosmetic purposes, for example for treating drying out of the skin, in particular after menopause, or for dermatological purposes, for example for the treatment of disorders associated with oligoseborrheic dry skin, in particular forms of dermatitis.

BACKGROUND OF THE INVENTION

Many women, from the age of thirty five, and more particularly after menopause, frequently complain of drying out of their skin, and of the manifestations of discomfort or unaesthetic manifestations which result therefrom (desquamation, dull complexion, atonia of the skin). Now, this drying out is due, as is now known, to a decrease in the production of sebum with age.

Moreover, children in whom the sebaceous function is not yet active often exhibit signs of dry skin.

Sebum is the natural product of the sebaceous gland which, along with the sweat produced by the eccrine or aprocrine glands, constitutes a natural moisturizer for the epidermis. It consists essentially of a more or less complex mixture of lipids. Conventionally, the sebaceous gland produces squalene, triglycerides, aliphatic waxes, cholesterol waxes and possibly free cholesterol (Stewart, M. E., *Semin. Dermatol.* 11, 100–105 (1992)). The action of bacterial lipases converts a varying portion of the triglycerides to free fatty acids.

The sebocyte constitutes the competent cell of the sebaceous gland. The production of sebum is associated with the programme of terminal differentiation of this cell. During this differentiation, the metabolic activity of the sebocyte is essentially centred around the biosynthesis of lipids (lipogenesis), and more precisely around the neosynthesis of fatty acids and the squalene.

A compound making it possible to stimulate the production of the lipids constituting sebum, by the cells of the sebaceous gland (sebocytes), would therefore be of definite value for the treatment of oligoseborrheic dry skin, i.e. skin exhibiting a sebum content of less than 100 $\mu g/cm^2$ on the forehead.

For this purpose, in patent U.S. Pat. No. 4,496,556, the use of DHEA, a steroid secreted by the adrenal glands, or esters thereof, administered topically, has been proposed in order to increase the production of sebum.

However, for regulatory reasons, it is not always possible to use this type of compound in the cosmetics field. In addition, it is not sufficiently effective on oligoseborrheic skin. There remains therefore the need to have cosmetically acceptable compounds which make it possible to effectively stimulate the sebaceous function for the purpose of treating oligoseborrheic dry skin.

DETAILED DESCRIPTION OF THE INVENTION

The inventors have discovered, with surprise, that some sapogenins make it possible to satisfy this need.

Sapogenins are compounds resulting from the acid hydrolysis (generally in the presence of hydrochloric acid or sulphuric acid in boiling aqueous medium) or enzyme hydrolysis (generally for approximately 5 days at approximately 37° C.), conventionally followed by extraction with an apolar organic solvent, of saponosides, which have functionalized heterocides, of very high molecular weight, present in the tubers of certain plants. As sources of saponosides, mention may be made of: the plants of the family Dioscoreaccae, such as *Dioscorea composita, Dioscorea deltoides, Dioscorea floribunda, Dioscorea sylvatica, Dioscorea spiculiflora* and *Dioscorea villosa*, which are rich in dioscin; and the plants of the Agave family.

Among the sapogenins, medicagenic acid and Medicago extracts containing same have been described as useful in the treatment of dry skins resulting from insufficient cell renewal (U.S. Pat. No. 5,273,149). It was not suggested however that other sapogenins, such as diosgenin and hecogenin, could have any effect on oligoseborrheic dry skins. This type of skin requires indeed using compounds that stimulate sebum production.

Similarly, FR-2 802 412 discloses a composition intended to moisturize in particular the skin, after exposure to infrared radiation. The composition contains, as active principle, a placental extract and also, as antimicrobial and anti-inflammatory agents, sapogenins, including ruscogenin and hederagenin. However, these compositions are applied to skin which has been dehydrated by evaporation of water due to the heating caused by exposure to infrared radiation, and not to oligoseborrheic skin.

Diosgenin has already been described as an anti-inflammatory (Yamada et al., *Am. J. Physiol.,* 273:G355-G364, 1997), as a slimming agent, by virtue of its action on adipocytes (WO 00/30603), as a collagenase inhibitor and as an antimicrobial agent which can be used in the treatment of various pathological conditions with an infectious component, including acne and seborrheic dermatitis (DE-198 41 795).

Moreover, the inventors have described various compositions comprising sapogenins, including diosgenin, which can be used, among others, in the treatment of cutaneous aging (U.S. Ser. No. 2002/0028186; U.S. Pat. No. 6,331,535; FR-2 811 561; and FR-2 811 567).

Thus, to the inventors' knowledge, it has never been suggested to use diosgenin or hecogenin in the treatment of oligoseborrheic dry skins.

In addition, extracts of *Dioscorea tokoro*, which contain dioscin, have been described as effective for moisturizing the skin and thus softening it. Thus, document JP-10 194 947 discloses an extract of *Dioscorea tokoro* prepared by extraction using water, alcohol or acetone at a temperature of between 0 and 50° C., preferably 0° C. This extract is described as being of use for improving the suppleness and the moisturization of the skin due to the glycoproteins which it contains. It is also thought to have a suppressive effect on sebaceous secretion.

As regards document JP-2000 143 488, it discloses a composition for preventing and improving drying out of the skin, comprising an extract of a plant chosen from a long list, including *Dioscorea tokoro* maquino and *Dioscorea gracillima* miq., which are sources of saponisides. Here again, the extraction method comprises simply immersing the plant in a solvent at ambient temperature, followed by steps of filtration and of drying, and the extract thus obtained can be considered as containing the saponosides of the plant.

Similarly, document WO 00/13693 describes an anti-pollution plant complex having a moisturizing effect, which contains in particular saponoside-containing plants as anti-oxidants. These plants are extracted by grinding, maceration in an aqueous-alcoholic solvent at less than 50° C. and filtration.

Thus, the extraction methods described in these documents do not make it possible to obtain compositions containing sapogenins (including diosgenin), since they do not comprise an acid hydrolysis or enzyme hydrolysis step. The compositions therefore contain only saponosides (including dioscin).

One subject of the present invention is therefore the (cosmetic) use of a sapogenin chosen from diosgenin and hecogenin, or of a plant extract containing at least one of these sapogenins, for example as an agent for the treatment of oligoseborrheic dry skin or of a dry scalp.

Another subject of the invention is a method for the dermatological treatment of disorders associated with oligoseborrheic dry skin, such as forms of dermatitis, comprising applying to said skin at least one sapogenin, chosen from diosgenin and hecogenin, or of a plant extract containing same.

Another subject of the invention is a method for the (cosmetic) treatment of a dry skin or scalp, comprising topically applying to said skin or scalp at least one sapogenin chosen from diosgenin and hecogenin, or a plant extract containing same, in a physiologically acceptable medium.

By "oligoseborrheic dry skins", it is meant in the sense of the present invention skins exhibiting a sebum content of less than 100 $\mu g/cm^2$ on the forehead at midday. These types of skins are frequent after menopause, so the composition according to this invention is preferably applied to skin of post-menopausal women.

The sapogenin used according to the invention is chosen from diosgenin and hecogenin. Diosgenin is in particular available from the company SABINSA under the commercial name Diosgenin®.

The expression "plant extracts" is intended to mean any plant extract containing one or more of these sapogenins, after treatment intended to hydrolyse the saponosides, such as an extract of *Dioscorea*, which contains diosgenin, or an extract of agave leaf containing hecogenin and tigogenin.

Thus, diosgenin can be extracted from the tubers of certain *Dioscorea*, as previously indicated, using a method comprising successively: hydrolysis, under hot conditions, of the heterosides in inorganic acid medium (optionally after fermentation and drying of the tubers); and filtration of the insoluble fraction, which is then neutralized, washed and treated with an apolar solvent. Other extraction methods can, however, be used.

The *Dioscorea* varieties containing dioscin, a precursor of diosgenin, are listed in the publication by Franklin W. MARTIN, The Species of *Dioscorea* Containing Sapogenin, *Econ. Bot.*, Vol. 23, 373–384 (1969), to which reference may be made.

Among these, mention may be made of the *Dioscorea composita*, *Dioscorea deltoides*, *Dioscorea floribunda*, *Dioscorea sylvatica*, *Dioscorea spiculiflora* and *Dioscorea villosa* species. The extract used according to the invention is preferentially prepared from plant material originating from the *Dioscorea villosa* and *Dioscorea opposita* species. Such an extract is in particular available from the company ACTIVE ORGANICS under the commercial names Actigen Y® and Actiphyte Mexican Wild Yam®. It can, as a variation, be obtained from the company OSST under the commercial name Wild Yam P. E.® or from the company ALBAN MÜLLER under the commercial name Extrait sec igname sauvage® [wild yam dry extract].

Hecogenin is available from the company SIGMA. It can also be obtained by extraction of leaves from Agave of the *Hechtia texensis* species, according to a method similar to that described above for diosgenin. An Agave extract can be obtained from the company COSMETOCHEM under the commercial reference Herbasol Extract Agave®.

The amount of sapogenin which can be used according to the invention depends of course on the desired effect and can therefore vary within a large range, this amount being within the skill of the ordinary artisan in view of this disclosure.

To give an order of magnitude, the sapogenin, or the plant extract containing sapogenin, can be used in an amount representing from 0.0001% to 5% of the total weight of a composition, preferentially in an amount representing from 0.01% to 1.5% of the total weight of the composition.

The composition according to the invention is preferably one generally suitable for topical application to the skin and/or the scalp and it therefore preferably contains a physiologically acceptable medium, i.e. a medium compatible with the skin, its superficial appendages (eyelashes, nails, hair) and/or the mucous membranes.

For topical application to the skin, this composition may be provided in any (pharmaceutical) form normally used in the cosmetics and dermatological fields, and it may in particular be in the form of an aqueous, optionally gelled, solution, of a dispersion of the optionally two-phase lotion type, of an emulsion obtained by dispersion of a fatty phase in an aqueous phase (O/W) or vice versa (W/O), of a triple emulsion (W/O/W or O/W/O) or of a vesicular dispersion of the ionic and/or nonionic type. These compositions may be prepared according to the usual methods. According to this invention, a composition in the form of an oil-in-water emulsion is preferably used.

This composition may be more or less fluid and have the appearance of a white or coloured cream, an ointment, a milk, a lotion, a serum, a paste, a mousse. It may optionally be applied in the form of an aerosol. It may also be provided in solid form, in particular in the form of a stick. It may be used as a care product and/or as a make-up product for the skin. It may also be used as a shampoo or a conditioner.

The composition used according to the invention may also contain adjuvants which are used in the cosmetics field, such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants may be those conventionally used in the field considered and, for example, from 0.01 to 20% of the total weight of the composition. These adjuvants, depending on their nature, can be introduced into the fatty phase, into the aqueous phase or into the lipid vesicles. In any event, these adjuvants, and the proportions thereof, will preferably be chosen so as not to damage the desired properties of the sapogenins or of the plant extracts according to the invention.

When the composition used according to the invention is an emulsion, the proportion of the fatty phase may range from 5 to 80% by weight, and preferably from 5 to 50% by weight, relative to the total weight of the composition. The oils, the emulsifiers and any co-emulsifiers used in the composition in the form of an emulsion may be chosen from those conventionally used in the field considered. The emulsifier and the co-emulsifier may be present, in the composition, in a proportion ranging from 0.3 to 30% by weight, and preferably from 0.5 to 20% by weight, relative to the total weight of the composition, for example.

Useful oils which can be used in the invention include mineral oils (liquid petroleum jelly), oils of plant origin (avocado oil, soya bean oil), oils of animal origin (lanolin), synthetic oils (perhydrosqualene), silicone oils (cyclomethicone) and fluoro oils (perfluoropolyethers). Fatty alcohols (cetyl alcohol), fatty acids, and waxes (carnauba wax, ozokerite) may also be used as fatty substances.

Useful emulsifiers and co-emulsifiers which can be used in the invention include for example, of esters of fatty acid and of polyethylene glycol, such as PEG-100 stearate, and esters of fatty acid and of glycerol, such as glyceryl stearate.

As hydrophilic gelling agents, mention may in particular be made of carboxyvinyl polymers (carbomer), acrylic copolymers, such as acrylate/alkyl acrylate copolymers, polyacrylamides, polysaccharides, natural gums and clays, and, as lipophilic gelling agents, mention may be made of modified clays such as bentones, metal salts of fatty acids, hydrophobic silica and polyethylenes.

As active agents, it will be advantageous to introduce into the composition used according to the invention at least one compound chosen from: desquamating agents; moisturizers; anti-inflammatories or calmants; and agents stimulating keratinocyte proliferation and/or differentiation.

In fact, the stimulation of seborrhea by the sapogenins according to the invention may, in some individuals, provide an area of proliferation for the resident microflora of the follicular ostium (propionibacterium acnes in particular), thus causing considerable hydrolysis of the triglycerides of the sebum to free fatty acids and the reduction of the unsaturations of the polyunsaturated fatty acids (linoleic acid in particular). These two phenomena may contribute to a keratinization of the infundibulum and to formation of a microcomedone. This may degenerate into a comedone, plugging and dilating the pore in an unaesthetic manner. At a more advanced stage, this plug may diverge towards an inflammatory acne lesion.

The addition of desquamating agents or agents regulating keratinocyte proliferation or differentiation to the composition according to the invention makes it possible to avoid the formation of these comedones. Similarly, antibacterial or bacteriostatic agents make it possible to obtain the same effect, by moderating proliferation of the resident microflora.

In addition, moisturizers may complete the effect obtained using the sapogenins according to the invention, and anti-inflammatories or calmants are of use for improving the comfort of oligoseborrheic dry skin.

The invention will now be illustrated with the following nonlimiting examples. In these examples, the amounts are given as weight percent.

EXAMPLES

Example 1

Demonstration of the Activity of the Sapogenin on the Lipogenase

Hecogenin and diosgenin, provided by SIGMA, were tested on a model of immortalized human sebocytes in culture, derived from the SZ95 line described in C. C. Zouboulis, H. Seltmann, H. Neitzel & C. E. Orfanos, Establishment and Characterization of an Immortalized Human Sebaceous Gland Cell Line, *J. Invest. Dermatol.*, 113, 1011–1020 (1999).

The test consisted in measuring the amount of lipids produced by the sebocytes of the line (at confluency), in the presence or absence of active agents, diluted in DMSO such that the final amount of DMSO in the culture medium is 0.1%. After treatment for two days, the adherent cells are treated with Nile Red (1 $\mu$g/ml). The lipid content is then quantified by measuring the fluorescence of the dye (two excitation/emission couples: 485–540 nm for the neutral lipids and 540–620 nm for the non-neutral lipids). The results are given for the total lipids (combination of the two measurements).

The experiment was carried out in triplicate (assay products and control) in a 96-well plate and repeated three times.

The results are given in the table below:

| PRODUCT | VARIATION IN LIPIDS (compared to control) |
|---|---|
| Hecogenin (0.1 $\mu$M) | +5% |
| Diosgenin (0.1 $\mu$M) | +4% |

As emerges from this table, hecogenin and diosgenin induce an increase in the sebocytic lipogenesis.

In addition, in the same test, DHEA, tested at a concentration 100 times greater (10 $\mu$M), only produced an increase of 13% in the lipid content of the sebum, while being inactive at the dose of 0.1 $\mu$M. The sapogenins used according to the invention are therefore more effective than DHEA.

Example 2

Cosmetic and Dermatological Compositions

These compositions are prepared in a manner which is conventional to those skilled in the art. The amounts given in these examples are indicated as weight percents.

| A. Lotion | |
|---|---|
| Diosgenin | 1% |
| Salicylic acid | 1% |
| Propylene glycol | 5% |
| Alcohol | 87% |
| Water | qs 100% |

This lotion can be used in the evening to reboost sebaceous function.

| B. Cream | |
|---|---|
| Hecogenin | 1% |
| n-octanoyl-5-salicylic acid | 1% |
| Methylparaben | 0.1% |
| Propylparaben | 0.1% |
| Lanolin | 5% |
| Liquid petroleum jelly | 4% |
| Sesame oil | 4% |
| Cetyl alcohol | 5% |
| Glyceryl monostearate | 2% |
| Triethanolamine | 1% |
| Propylene glycol | 5% |
| Carbomer 940 | 0.1% |
| Water | qs 100% |

This cream, used as twice-daily applications, makes it possible to revive the radiance of dry skin.

| C. Ointment | |
|---|---|
| Diosgenin | 1% |
| Salicylic acid | 1% |
| Glyceryl monostearate | 3% |
| Propylene glycol | 12% |
| Petrolatum | 82.9% |
| Water | qs 100% |

| D. Gel | |
|---|---|
| Diosgenin | 1% |
| Salicylic acid | 1% |
| Hydroxypropylcellulose | 1% |
| PPG-12-buteth-16 | 2% |
| Triethanolamine | 0.2% |
| Propylene glycol | 5% |
| Alcohol | 45% |
| Carbomer 940 | 0.2% |
| Water | qs 100% |

| E. Oil-in-water emulsion | |
|---|---|
| Diosgenin | 0.3% |
| Lyophilized extract of rosemary | 0.2% |
| Glyceryl stearate | 2% |
| Polysorbate 60 | 1% |
| Stearic acid | 1.4% |
| Triethanolamine | 0.7% |
| Carbomer | 0.4% |
| Olive oil | 12% |
| Liquid fraction of karite butter | 12% |
| Octyldodecanol | 6% |
| Isononyl isononanoate | 10% |
| Antioxidant | 0.05% |
| Fragrance | 0.5% |
| Preserving agent | 0.3% |
| Water | qs 100% |

| F. Cream | |
|---|---|
| Diosgenin | 0.5% |
| Retinol | 0.1% |
| Glycerol | 3% |
| Xanthan gum | 0.1% |
| Oxyethylenated sorbitan stearate | 0.9% |
| PEG-100 stearate and glycerol stearate | 2.1% |
| Cetyl alcohol | 2.60% |
| Isononyl isononanoate | 11% |
| Octyldodecanol | 15% |
| Butylhydroxytoluene | 0.1% |
| Octocrylene | 2% |
| Triethanolamine | 0.3% |
| Tocopherol acetate | 1% |
| Preserving agents | 0.6% |
| Water | qs 100% |

-continued

| G. Cream | |
|---|---|
| Diosgenin | 0.3% |
| O-octanoyl-6'-D-maltose* | 2% |
| Triethanolamine | 0.3% |
| PEG-100 stearate and glyceryl stearate | 2.5% |
| PEG-50 stearate | 2.5% |
| Cetyl alcohol | 1% |
| Stearyl alcohol | 3% |
| Isononyl isononanoate | 20% |
| Propylparaben | 0.1% |
| Carbopol | 0.3% |
| Water | qs 100% |

*obtained as described in application EP-0 566 438

The above written description of the invention provides a manner and process of making and using it such that any person skilled in this art is enabled to make and use the same, this enablement being provided in particular for the subject matter of the appended claims and including the (cosmetic) use of a sapogenin chosen from diosgenin and hecogenin, or of a plant extract containing at least one of these sapogenins, as an agent for the treatment of oligoseborrheic dry skin or of a dry scalp, a method for the cosmetic treatment of a dry skin or scalp, comprising topically applying to said skin or scalp at least one sapogenin chosen from diosgenin and hecogenin, or a plant extract containing same, in a physiologically acceptable medium, and a method for the dermatological treatment of disorders associated with oligoseborrheic dry skin, including where these disorders are forms of dermatitis, comprising applying to said skin at least one sapogenin, chosen from diosgenin and hecogenin, or of a plant extract containing same. Also fully described and enabled are a method of treating oligoseborrheic dry skin or dry scalp, a method for the dermatological treatment of disorders associated with oligoseborrheic dry skin, and a method for treating dermatitis comprising applying a sapogenin selected from the group consisting of diosgenin, hecogenin and mixtures thereof.

All references, texts, patents, applications, publications, tests, standards, documents, etc., mentioned herein are incorporated herein by reference. Where a numerical range or limit is expressed, all values and subranges therewithin are expressly included as if specifically written out.

What is claimed is:

1. A method for treating oligoseborrheic dry skin or dry scalp, comprising applying thereto a sapogenin selected from the group consisting of diosgenin, hecogenin and mixtures thereof.

2. The method of claim 1, wherein said sapogenin is present in a composition, said composition further comprising a physiologically acceptable medium.

3. The method according to claim 1, wherein the sapogenin is hecogenin.

4. The method according to claim 1, wherein the sapogenin is diosgenin.

5. The method according to claim 1, wherein said sapogenin is present in a composition, and represents from 0.1 to 1.5% of the total weight of the composition, the composition further comprising a physiologically acceptable medium.

6. The method according to claim 5, wherein said composition further comprises at least one additive selected from the group consisting of a desquamating agent, a moisturizer, an anti-inflammatory or calmant, an agent which promotes keratinocyte proliferation and/or differentiation, and an antibacterial agent.

7. The method according to claim 5, wherein the composition is in the form of an oil-in-water emulsion.

8. The method according to claim 1, wherein the sapogenin is applied to the dry skin or dry scalp of post-menopausal women.

9. A method for treating oligoseborrheic dry skin or dry scalp according to claim 1, comprising applying thereto a plant extract comprising a sapogenin selected from the group consisting of diosgenin, hecogenin and mixtures thereof.

10. The method according to claim 9, wherein the plant extract is a *Dioscorea* extract.

* * * * *